(12) United States Patent
Fox

(10) Patent No.: US 7,345,208 B2
(45) Date of Patent: Mar. 18, 2008

(54) METHOD FOR MAKING AN ENERGETIC MATERIAL

(75) Inventor: Robert V. Fox, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 152 days.

(21) Appl. No.: 11/231,142

(22) Filed: Sep. 19, 2005

(65) Prior Publication Data

US 2007/0232840 A1 Oct. 4, 2007

(51) Int. Cl.
*C07C 205/06* (2006.01)
*C06B 25/08* (2006.01)

(52) U.S. Cl. .................................................. 568/935
(58) Field of Classification Search ................ 568/935
See application file for complete search history.

(56) References Cited

U.S. PATENT DOCUMENTS 3,799,993 A 3/1974 Hill et al.
6,177,033 B1 1/2001 Nauflett et al.
6,881,871 B1 4/2005 Davis

OTHER PUBLICATIONS

Ulrich et al., Formation of Energetic Materials Using Supercritical Fluids, Propellants, Explosives, Pyrotechnics 26, 168-173 (2001).

*Primary Examiner*—Yvonne Eyler
*Assistant Examiner*—Yevgeny Valenrod
(74) *Attorney, Agent, or Firm*—Wells St. John, P.S.

(57) ABSTRACT

A method for making trinitrotoluene is described, and which includes the steps of providing a source of aqueous nitric acid having a concentration of less than about 95% by weight; mixing a surfactant with the source of aqueous nitric acid so as to dehydrate the aqueous nitric acid to produce a source of nitronium ions; providing a supercritical carbon dioxide environment; providing a source of an organic material to be nitrated to the supercritical carbon dioxide environment; and controllably mixing the source or nitronium ions with the supercritical carbon dioxide environment to nitrate the organic material and produce trinitrotoluene.

21 Claims, 1 Drawing Sheet

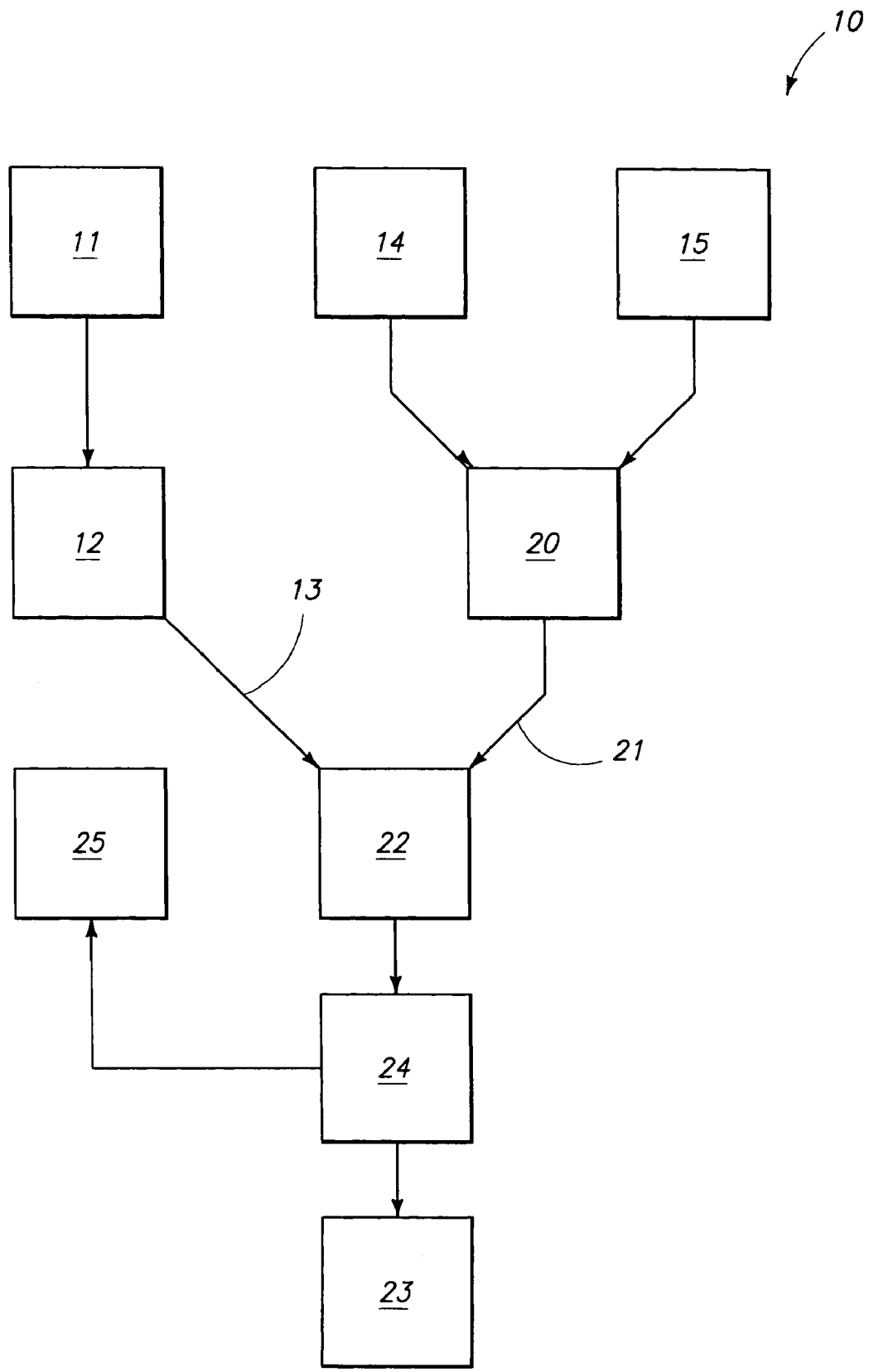

METHOD FOR MAKING AN ENERGETIC MATERIAL

GOVERNMENT RIGHTS

The United States Government has certain rights in this invention pursuant to Contract No. DE-AC07-051D14517 between the United States Department of Energy and Battelle Energy Alliance, LLC.

TECHNICAL FIELD

The present invention relates to a method for making an energetic material, and more specifically to a method wherein the nitration of an organic material takes place in a carbon dioxide environment, and which reduces the amount of spent acid generated from the nitration reaction, to produce a desired energetic material.

BACKGROUND OF THE INVENTION

The current commercial production of trinitrotoluene typically occurs by way of a nitration reaction of orthonitrotoluene (ONT), to dinitrotoluene (DNT), and the resulting trinitrotoluene (TNT). This chemical reaction typically occurs in a solution which normally comprises greater than about 70%, by weight, of sulfuric acid; approximately 1% to 5% by weight of nitric acid; and approximately about 1% to about 3% of orthonitrotoluene at temperatures of greater than about 65 degrees C. Under these reaction conditions, the sulfuric acid acts as both a solvent for the associated nitrotoluene, and as a dehydrating agent that sequesters water present in the reaction mixture. In the reaction noted above, the active nitrating agent is the nitronium ion ($NO_2^+$) that arises as an equilibrium product from the dissociation of the nitric acid. Increasing amounts of water in the reaction, referenced above, substantially prevents this dissociation. However, because sulfuric acid has a higher affinity for water, then does nitric acid at sulfuric acid concentrations of greater than about 70%, the nitric acid becomes dehydrated thus favoring the formation of the nitronium ion.

Those skilled in the art recognize that the nitronium ion ($NO_2^+$) is considered to be a very active nitrating species. As a general matter, the nitronium ion substantially indiscriminately nitrates organic compounds. In the prior art reaction discussed, above, however, it has long been recognized that the nitration of the organic materials and the formation of end products such as trinitrotoluene (TNT), in this manner, gives rise to significant quantities of spent and diluted sulfuric acid waste streams. This problem has long been recognized in the art and attempts have been made to address this problem by means of various teachings such as found at U.S. Pat. Nos. 6,177,033 and 6,881,871. The teachings of these patents incorporated by reference herein.

In the prior art commercial processes which have been utilized heretofore, the final product (TNT), and other organics such as dinitrotoluene, and unreacted orthonitrotoluene, are usually stripped from the remaining spent acid solutions. The spent acid solutions are then typically sent to an acid recovery plant where the sulfuric acid is dehydrated and recovered. As should be understood from this discussion, the manufacturing costs related to this spent acid recovery, and disposal of the associated waste material are quite considerable in the production of TNT.

Attempts have been made in the prior art to avoid the shortcomings attendant with the current methodology for producing energetic material such as trinitrotoluene (TNT). For example, in U.S. Pat. No. 6,177,033 to Nauflett, the inventors have disclosed a methodology where dinitrogen pentoxide ($N_2O_5$) which is produced through a number of different routes including phosphorous pentoxide, and ozonalysis, reacts with water to form $HNO_3$ which then dissociates to form nitronium ions. The nitronium ions are used for purposes of nitrating a target organic material. The difficulty in the approach, as disclosed in this reference, and which takes place within a carbon dioxide environment, is that $N_2O_5$ is very unstable and dissociates rapidly at room temperature. Consequently, in the methodology as described in Nauflett, the $N_2O_5$ must be manufactured onsite which creates various difficulties including obvious safety hazards. In the Nauflett patent the inventors acknowledge that a liquid carbon dioxide environment offers significant safety and environmental benefits over conventional nitrating agents, such as mixed acid, to manufacture energetic materials (Column 3, lines 53-63). They note, however, that nitric acid mixed with acetic acid or acetic anhydride can explode if not kept cold. They further acknowledge that the carbon dioxide environment serves as a dilutant for the nitration reactions in the acetic anhydride/nitric acid media.

Therefore, a method for making an energetic material in a carbon dioxide environment and which avoids the shortcomings attendant with the prior art practices and methodology utilized heretofore is the subject matter of the present application.

SUMMARY OF THE INVENTION

A first aspect of the present invention relates to a method for making an energetic material which includes the steps of providing a source of aqueous nitric acid having a concentration of less than about 95% by weight; mixing a surfactant with the source of the aqueous nitric acid so as to dehydrate the aqueous nitric acid to produce a source of nitronium ions; providing a carbon dioxide environment; providing a source of an organic material to be nitrated to the carbon dioxide environment; and controllably mixing the source of nitronium ions with the carbon dioxide environment to nitrate the organic material and produce a resulting energetic material.

Another aspect of the present invention relates to a method for making an energetic material which includes the steps of forming a carbon dioxide environment; providing a source of a nitrating agent; providing a source of a surfactant; providing a source of an organic material to be nitrated; and mixing the nitrating agent, surfactant and the organic material in the carbon dioxide environment to produce the energetic material.

Yet another aspect of the present invention relates to a method for making an energetic material which includes the steps of providing an organic material to be nitrated; providing a first source of carbon dioxide, and substantially dissolving the organic material in the first source of carbon dioxide to produce a first feed stream; providing a source of an organophosphorous surfactant which has at least about 6 to about 20 carbon atoms; providing a source of an aqueous nitric acid; providing a second source of carbon dioxide, and mixing the organophosphorous surfactant and the nitrating agent in the second source of carbon dioxide to produce a second feed stream; and combining the first and second feed streams together so as to facilitate the nitration of the organic material to form a resulting energetic material.

These and other aspects of the present invention will be described in greater detail hereinafter.

BRIEF DESCRIPTION OF THE DRAWINGS

Preferred embodiments of the invention are described below with reference to the following accompanying drawings:

FIG. 1 is a greatly simplified schematic representation of one arrangement for practicing the methodology of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Referring to FIG. 1, a generalized, schematic representation of an arrangement for practicing the method for making an energetic material of the present invention is generally indicated by the numeral 10. The methodology 10 of the present invention includes, as a first step, providing an organic material to be nitrated, and which is generally indicated by the numeral 11. In the present invention, the organic material to be nitrated 11 is typically selected from the group comprising orthonitrotoluene and dinitrotoluene. Those skilled in the art will recognize that this methodology may work with other material, and the methodology as disclosed is not limited to these two exemplary organic materials. In the methodology as seen in FIG. 1, the method includes, after the step of providing an organic material to be nitrated 11, a second step of providing a first source of carbon dioxide 12, and thereafter substantially dissolving the organic material 11 in the first source of carbon dioxide 12 to produce a resulting first feed stream 13. In the methodology as seen in FIG. 1, the step of providing a first source of carbon dioxide 12 includes providing the first source of carbon dioxide at a pressure of greater than about 900 PSI to about 5,000 PSI, and at a temperature of greater than about –30 degrees C. to less then about 85 degrees C., respectively. The method 10 further includes another step of providing a source of an organophosphorous surfactant 14 which has at least about 6 to about 20 carbon atoms. The organophosphorous surfactant is selected from the group comprising tributyl phosphate; tributyl phosphite; and tributyl phosphine oxide, and the hydroflurocarbon and/or perflurocarbon analogs thereof. In the arrangement as seen in FIG. 1, the methodology 10 includes another step of providing a source of aqueous nitric acid 15. In the arrangement as seen in FIG. 1, the methodology includes another step of providing a second source of carbon dioxide 20, and thereafter mixing the organophosphorous surfactant 14, and the aqueous nitric acid which acts as a nitrating agent 14, in the second source of carbon dioxide 20, to produce a resulting, second feed stream 21. The methodology 10 includes another step of combining the first and second feed streams together at a step 22, so as to facilitate the nitration of the organic material 11 to form a resulting energetic material which is subsequently recovered at 23. As should be understood, the step of providing the second source of carbon dioxide 20, includes providing the carbon dioxide at a pressure of about 900 PSI to about 5,000 PSI, and at a temperature of about –30 degrees C. to about 85 degrees C. In the arrangement as seen in FIG. 1, the step of providing a source of aqueous nitric acid includes providing a source of aqueous nitric acid having a concentration of less than about 95% by weight, and typically less than about 75% by weight. In the methodology as seen in FIG. 1, and after the step of combining the first and second feed streams 13 and 21 so as to facilitate the nitration of the organic material 11 to form the resulting material 22, the method includes another step of providing a third source of carbon dioxide 24, and removing and recycling any unreacted nitric acid; organophosphorous surfactant; and/or organic material 11 with the third source of carbon dioxide 24 and recycling these same materials at the step labeled 25.

In its broadest aspect, the present method for making an energetic material 10 includes the steps of providing a source of aqueous nitric acid 15 having a concentration of less than about 95% by weight; mixing a surfactant 14 with the source of the aqueous nitric acid so as to dehydrate the aqueous nitric acid to produce a source of nitronium ions 20; providing a carbon dioxide environment 12; providing a source of an organic material 11 to be nitrated to the carbon dioxide environment 12; and controllably mixing the source of nitronium ions with the carbon dioxide environment 22 to nitrate the organic material and produce a resulting energetic material 23. In the methodology 10 as described above, and as earlier discussed the surfactant 14, comprises an organophosphorous surfactant which is selected from the group comprising organophosphates; organophosphites; and organophosphine oxides, and the hydroflurocarbon and/or perflurocarbon analogs thereof, and which each have at least about 6 to about 20 carbon atoms. As presently contemplated, the organic material to be nitrated 11 is soluble, at least in part, in the carbon dioxide environment 12, and the step of controllably mixing the source of nitronium ions which is provided by the mixing of the nitric acid 15 with the organophosphorous surfactant 14 in the carbon dioxide environment 20 comprises, at step 22, bubbling the carbon dioxide having the dissolved organic material to be nitrated through the source of nitronium ions. In an alternative mode of practicing the present invention 10, the organic material 11 to be nitrated is not soluble in the carbon dioxide environment 12, and the step of controllably mixing the source of the nitronium ions comprises passing the source of the nitronium ions over the organic material to be nitrated. As presently contemplated, the step of providing the first and second carbon dioxide environments 12, and 20 respectively comprises providing a source of carbon dioxide at a pressure of about 900 PSI to about 5000 PSI, and at a temperature of –30 degrees C. to about 85 degrees C. As noted above, the controllable mixing of the source of nitronium ions, with the carbon dioxide environment, to nitrate the organic material 11 produces a resulting energetic material 23. The methodology as described above further includes a step of releasing the pressure, at least in part, from the carbon dioxide environments noted above, and recovering the energetic materials at step 23. In the arrangement as seen in FIG. 1, and as earlier discussed, the organic material 11 to be nitrated is selected from the group comprising orthonitrotoluene and dinitrotoluene, and the resulting energetic particle 23 comprises trinitrotoluene.

OPERATION

The operation of the described embodiments of the present invention are believed to be readily apparent and are briefly summarized at this point.

In the present invention a method 10 for making an energetic material 23 comprises the steps of forming a carbon dioxide environment 12, 20; providing a source of a nitrating agent 15; providing a source of a surfactant 14; providing a source of an organic material to be nitrated 11; and mixing the nitrating agent, surfactant, and the organic material in the carbon dioxide environment 22 to produce the energetic material 23. In the methodology as described above, the step of forming a carbon dioxide environment 12 comprises further steps of providing a first source of carbon dioxide 12, and dissolving the organic material 11 in the first source of carbon dioxide to produce a first feed stream 13; and providing a second source of carbon dioxide 20, and dissolving the nitrating agent 15, and the surfactant 14 in the second source of carbon dioxide to produce a second feed stream 21. In the methodology as seen, the step of mixing the nitrating agent, surfactant and the organic material in the carbon dioxide environment 12, 20 further comprises controllably mixing 22 the first and second feed streams 13, 21 to produce the energetic material 23. The present invention is further understood by means of the non-limiting example which is provided below.

EXAMPLE 1

An experiment was conducted wherein a 50:50 mixture of anhydrous tributylphosphate (TBP) and concentrated aqueous nitric acid having a concentration of approximately (70% by weight (15.8M) was supplied to a carbon dioxide environment which had a temperature of about 45 degrees C. and a pressure of about 3000 PSI. The carbon dioxide environment was substantially devoid of any water. The resulting mixture was miscible, appeared single-phase, and had a dark red color. In a first experiment, approximately 0.25 milliliters (0.0021 Moles) of orthonitrotoluene (ONT) was pipetted into a 5 milliliter high-pressure optical cell. Thereafter, approximately 0.6 milliliters of a 50:50 volume mixture of TBP and $HNO_3$ mixture (approximately 0.0018 Moles of TBP; 0.047 Moles of $HNO_3$) were added to an inline injection loop. The high-pressure optical cell and inline injection loop were then pressurized to a pressure of about 3000 PSI at 45 degrees C. with stirring. The subsequent reaction produced approximately 0.002 Moles of trinitrotoluene (TNT). In a second experiment, approximately 0.85 grams of solid dinitrotoluene (DNT) was weighed, and placed into a 5 milliliter high-pressure optical cell. Thereafter, approximately 0.6 milliliters of a 50:50 volumetric mixture of TBP and $HNO_3$ (0.018 Moles TBP; 0.047 Moles $HNO_3$) were added to an inline injection loop. The high-pressure optical cell and inline injection loop were pressurized to about 3000 PSI at a temperature of 45 degrees C. with stirring. The resulting reaction produced approximately 0.045 Moles of TNT. In both experiments, noted above, a UV-VIS spectrophotometer was used to analyze the contents of the optical cell while it was pressurized. In both experiments the pressure was slowly released and white crystalline material formed as the solvent evaporated. The white material was subsequently analyzed and found to be trinitrotoluene.

Therefore, the methodology for making an energetic material of the present invention can be employed to manufacture end products such as TNT, while avoiding many of the serious manufacturing difficulties which relate to the prior art practices which have been utilized heretofore.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A method for making trinitrotoluene, comprising:
   providing a source of aqueous nitric acid having a concentration of less than about 95% by weight;
   mixing a organophosphorous surfactant with the source of the aqueous nitric acid so as to dehydrate the aqueous nitric acid to produce a source of nitronium ions;
   providing a supercritical carbon dioxide environment;
   providing a source of an organic material to be nitrated to the supercritical carbon dioxide environment, the organic material being selected from the group comprising orthonitrotoluene and dinitrotoluene; and
   controllably mixing the source of nitronium ions with the supercritical carbon dioxide environment to nitrate the organic material and produce trinitrotoluene.

2. A method as claimed in claim 1, and wherein surfactant comprises an organophosphorous surfactant which is selected from the group comprising organophosphates; organophosphites; and organophosphine oxides, and the hydrofluorocarbon and/or perflurocarbon analogs thereof, and wherein each of the organophosphorous surfactants have at least 6 to about 20 carbon atoms.

3. A method a claimed in claim 1, and wherein the organic material to be nitrated is soluble, at least in part, in the supercritical carbon dioxide environment, and wherein the step of controllably mixing the source of nitronium ions with the supercritical carbon dioxide environment comprises bubbling the carbon dioxide having the dissolved organic material to be nitrated through the source of nitronium ions.

4. A method as claimed in claim 1, and wherein the organic material to be nitrated is not soluble in the supercritical carbon dioxide environment, and wherein the step of controllably mixing the source of nitronium ions comprises passing the source of the nitronium ions over the organic material to be nitrated.

5. A method as claimed in claim 1, and wherein the step of providing the supercritical carbon dioxide environment comprises providing a source of carbon dioxide at a pressure of about 900 PSI to about 5000 PSI, and at a temperature of −30 degrees C. to about 85 degrees C.

6. A method as claimed in claim 5, and wherein after the step of controllably mixing the source of nitronium ions with the supercritical carbon dioxide environment, the method further comprises:
   releasing the pressure, at least in part, from the supercritical carbon dioxide environment; and
   recovering trinitrotoluene.

7. A method for making trinitrotoluene, comprising:
   forming a supercritical carbon dioxide environment;
   providing a source of a nitrating agent;
   providing a source of a organophosphorous surfactant;
   providing a source of an organic material to be nitrated, the organic material being selected from the group comprising orthonitrotoluene and dinitrotoluene; and
   mixing the nitrating agent, surfactant and the organic material in the supercritical carbon dioxide environment to produce trinitrotoluene.

8. A method as claimed in claim 7, and wherein the step of forming a supercritical carbon dioxide environment further comprises:
   providing a first source of supercritical carbon dioxide and dissolving the organic material in the first source of supercritical carbon dioxide to produce a first feed stream; and providing a second source of supercritical carbon dioxide and dissolving the nitrating agent and the organophosphorous surfactant in the second source of supercritical carbon dioxide to produce a second feed stream.

9. A method as claimed in claim 8, and wherein the step of mixing the nitrating agent, surfactant and the organic material in the supercritical carbon dioxide environment further comprises:
controllably mixing the first and second feed streams to produce trinitrotoluene.

10. A method as claimed in claim 8, and wherein the first and second sources of supercritical carbon dioxide are supplied at a pressure of greater that about 900 PSI; and a temperature of greater than about −30 degrees C. to about 85 degrees C., respectively.

11. A method as claimed in claim 7, and wherein the nitrating agent comprises aqueous nitric acid which has a concentration of about 50% by weight to about 95% by weight.

12. A method as claimed in claim 7, and wherein the surfactant comprises an organophosphorous surfactant which is selected from the group comprising tributyl phosphate; tributyl phosphite; tributyl phosphine oxide, and the hydroflurocarbon and/or perflurocarbon analogs thereof.

13. A method as claimed in claim 7, and wherein the surfactant comprises an organophosphate, phosphite, and/or phosphine oxide and the hydroflurocarbon and/or perflurocarbon analogs thereof, and which further has at least about 6 to about 20 carbon atoms.

14. A method as claimed in claim 8, and further comprising:
after the step of mixing the nitrating agent, surfactant, and organic material in the supercritical carbon dioxide environment to produce trinitrotoluene, providing a third source of supercritical carbon dioxide;
removing and recycling any unreacted nitrating agent, surfactant, and/or organic material with the third source of supercritical carbon dioxide; and
recovering the trinitrotoluene.

15. A method for making trinitrotoluene comprising:
providing an organic material to be nitrated, the organic material being selected from the group comprising orthonitrotoluenen and dintrotoluene;
providing a first source of supercritical carbon dioxide, and substantially dissolving the organic material in the first source of supercritical carbon dioxide to produce a first feed stream;
providing a source of an organophosphorous surfactant which has at least about 6 to about 20 carbon atoms;
providing a source of an aqueous nitric acid;
providing a second source of supercritical carbon dioxide, and mixing the organophosphorous surfactant and the nitrating agent in the second source of supercritical carbon dioxide to produce a second feed stream; and
combining the first and second feed streams together so as to facilitate the nitration of the organic material to form trinitrotoluene.

16. A method as claimed in claim 15, and wherein the organophosphorous surfactant is selected from the group comprising tributyl phosphate; tributyl phosphite; and tributyl phosphine oxide, and the hydroflurocarbon and/or perflurocarbon analogs thereof.

17. A method as claimed in claim 15, and wherein the aqueous nitric acid is provided at a concentration of less than about 95%, by weight.

18. A method as claimed in claim 15, and wherein the aqueous nitric acid is provided at a concentration of less than about 70%, by weight.

19. A method as claimed in claim 15, and further comprising:
after the step of combining the first and second streams together to form trinitrotoluene;
recovering the trinitrotoluene; and
recycling any unreacted organic material, organophosphorous surfactant, and nitric acid.

20. A method as claimed in claim 19, and wherein the step of recovering the trinitrotoluene is performed by precipitating the trinitrotoluene.

21. A method as claimed in claim 19, and wherein the first and second sources of supercritical carbon dioxide are provided at a pressure of about 900 PSI to about 5000 PSI, and at a temperature of −30 degrees C. to about 85 degrees C., and wherein the step of precipitation comprises, at least in part, substantially releasing the pressure from the first and second sources of supercritical carbon dioxide.

* * * * *